United States Patent [19]

Liu

[11] Patent Number: 4,543,426
[45] Date of Patent: Sep. 24, 1985

[54] HERBICIDAL COMPOUNDS
[75] Inventor: Kou-Chang Liu, Wayne, N.J.
[73] Assignee: GAF Corporation, Wayne, N.J.
[21] Appl. No.: 568,999
[22] Filed: Jan. 9, 1984
[51] Int. Cl.$^4$ ............................................. C07C 87/60
[52] U.S. Cl. ...................................... 564/442; 71/121
[58] Field of Search ........................... 564/442; 71/121
[56] References Cited
U.S. PATENT DOCUMENTS
4,339,457 7/1982 Plummer et al. .................... 424/274

Primary Examiner—Charles F. Warren
Assistant Examiner—Joseph A. Boska
Attorney, Agent, or Firm—Marilyn J. Maue; Joshua J. Ward

[57]    ABSTRACT

A compound of the formula:

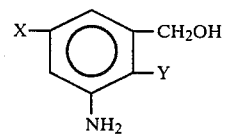

where X and Y are independently chlorine or trifluoromethyl.

6 Claims, No Drawings

HERBICIDAL COMPOUNDS

BACKGROUND OF THE INVENTION

1. Field of the Invention

This invention relates to novel compounds which are active herbicides having high selectivity to soybean and graminae crops including corn, wheat and rice.

2. Description of the Prior Art

Certain dichloroanilines have shown generally high activity as plant irradicants and herbicides. Foremost of these are discussed in U.S. Pat. Nos. 3,174,842; 3,332,769; and 4,046,758. However, the herbicidal effectiveness and selectivity of a dihaloaniline having substitution by different functional groups cannot be predicted from an examination of its basic chemical structure or homologous relationship. Often structurally related aromatic compounds have markedly different weed control abilities and crop selectivity.

While many of the dihaloanilines exhibit high plant eradicating properties, they show little if any phytotoxic selectivity for certain commercial crops, such as graminae in either pre-emergence or post-emergence applications. Hence, their range of application is limited unless rates are reduced to such a level that they become ineffectual on certain weed species or repeated applications are required throughout the planting and growing seasons.

Accordingly, it is an object of this invention to provide a herbicide having exceptionally high herbicidal activity in a single application while simultaneously showing good crop selectivity towards commercial graminae crops.

Another object of this invention is to provide a herbicide which can be economically produced and applied to crops in small amounts which are non-contaminating to the soil.

These and other objects will become apparent to those skilled in the art.

SUMMARY OF THE INVENTION

In accordance with the present invention, there is provided novel herbicidal halogenated hydroxy alkyl aniline having the formula

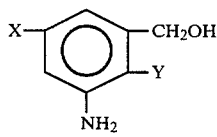

where X and Y are independently chlorine or trifluoromethyl.

Examples of the compounds of this invention embraced within the formula include:
2,5-dichloro-3-hydroxymethyl aniline
2-chloro-5-trifluoromethyl-3-hydroxymethyl aniline
2,5-trifluoromethyl-3-hydroxymethyl aniline and
2-trifluoromethyl-5-chloro-3-hydroxymethyl aniline.

DETAILED DESCRIPTION OF THE INVENTION

The halogenated hydroxymethyl anilines of this invention are preferably prepared by reacting the correspondingly halogenated amino benzoic acid with a suitable reducing agent such as borontrifluoride-tetrahydrofuran at a temperature of from about 0° to about 50° C. under atmospheric pressure.

The compounds of this invention are useful both as pre-emergent and post-emergent herbicides. Among the crops on which the compounds may be advantageously employed are, for example, soybean, rice, corn, cotton, wheat, sorghum, peanuts, safflower, beans, peas, carrots, and other cereal crops.

The present halogenating hydroxyalkyl anilines may be applied in any amount which will give the required control of weeds. A preferred rate of application of the benzoates is from 0.05 to 8 lbs. per acre. In practical application, the compounds may be applied in solid, liquid or in vaporized form, or, as an active ingredient in a herbicidal composition or formulation which comprises a carrier and/or a surfactant. A generally accepted carrier is a substance which can be used to dissolve, disperse or diffuse the herbicidal components in the composition. Non-limiting examples of liquid carriers include water, organic solvents such as alcohols, ketones, halogenated hydrocarbons, aromatic hydrocarbons, ethers, amides, esters, nitriles, mineral oils, methyl pyrrolidone, polyvinylpyrrolidone and the like. Non-limiting examples of solid carriers include Kaolin, bentonite, talc, diatomaceous earth, vermiculite, clay, gypsum, grain and seed hulls, ground corn cobs and the like. In addition to a carrier, it is usually desirable to add to the composition additives such as emulsifying agents, wetting agents, binding agents, stabilizer and the like. The compounds may be formulated, for example, as a dust, wettable powders, emulsifiable concentrates, granular formulations or aerosols.

The halogenated hydroxyalkyl anilines herein described may be applied along with plant growth regulators, insecticides, fungicides, nematocides and fertilizers. They may be applied in combination with one or more other herbicides. Non-limiting examples of other herbicides which can be incorporated with the phenoxybenzoates of this invention are anilides, such as N-methoxymethyl (2,6-diethylphenyl) chloroacetamide; dinitroanilines, such as α,α,α-trifluoro-2,6-dinitro-N,N-di-propyl-p-toluidine; carboxylic acids and derivatives; triazines; substituted ureas; carbamates; thiocarbamates; uracils; heterocycles, organo phosphorous compounds and the like.

Having thus generally described the invention, reference is now had to the following examples which represent preferred embodiments but which are not to be construed as limiting to the scope of the invention as more broadly set forth hereinabove and in the appended claims.

EXAMPLE 1

Preparation of 3-Amino-2,5-Dichlorobenzyl Alcohol

Into a 1 liter three-neck flask was introduced 40 g (0.19 mole) of 3-amino-2,4-dichlorobenzoic acid and 150 ml of tetrahydrofuran. The solution was cooled to 8°–10° C. in an ice bath. A borontrifluoride-tetrahydrofuran (1M) solution (280 ml) was added dropwise over a period of 1 hr. After being stirred at 8° C. for an additional 1 hr. the solution was allowed to warm up slowly to room temperature. The reaction flask was then cooled again in an ice bath and 50 ml of water was added through a dropping funnel. The mixture was taken into 1 liter of methylene chloride and washed once with NaHCO₃ and twice with water, then dried over calcium sulfate. The methylene chloride solution afforded 19.2 g of crude solid product, mp 111–121. Five grams of the crude solid was recrystallized from acetonitrile to yield 4.2 g of 3-amino-2,5-dichlorobenzyl alcohol; mp 121–127; nmr (DMSO-d6) δ4.50 (D, 2H), 5.34 (t, 1H), 5.52 (S, 2H), 6.73 (S, 2H); ir (CHCl$_3$) 3490, 3380, 3240, 1630 and 1598 Cm$^{-1}$.

The 3-amino-2-chloro-5-trifluoromethyl benzyl alcohol, 3-amino-5-chloro-2-trifluoromethyl benzyl alcohol and 3-amino-2,5-trifluoromethyl benzyl alcohol are prepared according to this example, except that the above benzoic acid is substituted with the benzoic acid having the described substitution, i.e. 3-amino-2-chloro-5-trifluoromethyl-, 3-amino-5-chloro-2-trifluoromethyl-, or 3-amino-2,5-trifluoromethyl- substituted benzoic acid.

EXAMPLE 2

Herbicidal Tests

Tests were made on species of representative monocotyledonous and dicotyledonous plants at a rate of 5 lbs/acre, 3-amino-2,5-dichlorobenzyl alcohol in aqueous solution was applied immediately after seeding with plants shown in the following table. The response was evaluated after 2 weeks on a scale of 0 to 9 where 0 represents no injury and 9 represents complete kill.

TABLE

| Plant Species | Toxicity |
| --- | --- |
| Morning Glory | 8 |
| Mustard | 9 |
| Pigweed | 9 |
| Foxtail | 9 |
| Japanese Millet | 9 |
| Crabgrass | 9 |
| Soybean | 5 |
| Corn | 6 |
| Wheat | 3 |
| Rice | 5 |

While the invention has been described with particular reference to a certain preferred embodiment thereof, however, it will be understood that certain modifications can be made, such as the substitution in Example 2 of any of the other halogenated hydroxymethyl anilines which compounds provide similar results.

What is claimed is:

1. The process which comprises treating an undesirable plant species with an effective phytotoxic amount of a herbicide of the formula:

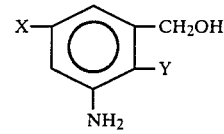

where X and Y are independently chlorine or trifluoromethyl.

2. The process of claim 1 wherein at least one of X and Y of said herbicide is trifluoromethyl.

3. The process of claim 1 wherein X and Y of said herbicide are chlorine.

4. The process of claim 1 wherein X and Y of said herbicide are trifluoromethyl.

5. A herbicide of the formula:

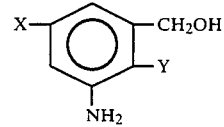

where X and Y are independently chlorine or trifluoromethyl and wherein at least one of X and Y is trifluoromethyl.

6. The herbicide of claim 5 wherein X and Y are trifluoromethyl.

* * * * *